Nov. 1, 1938. E. R. DRAMM Plant Pat. 301
ROSE
Filed Feb. 14, 1938
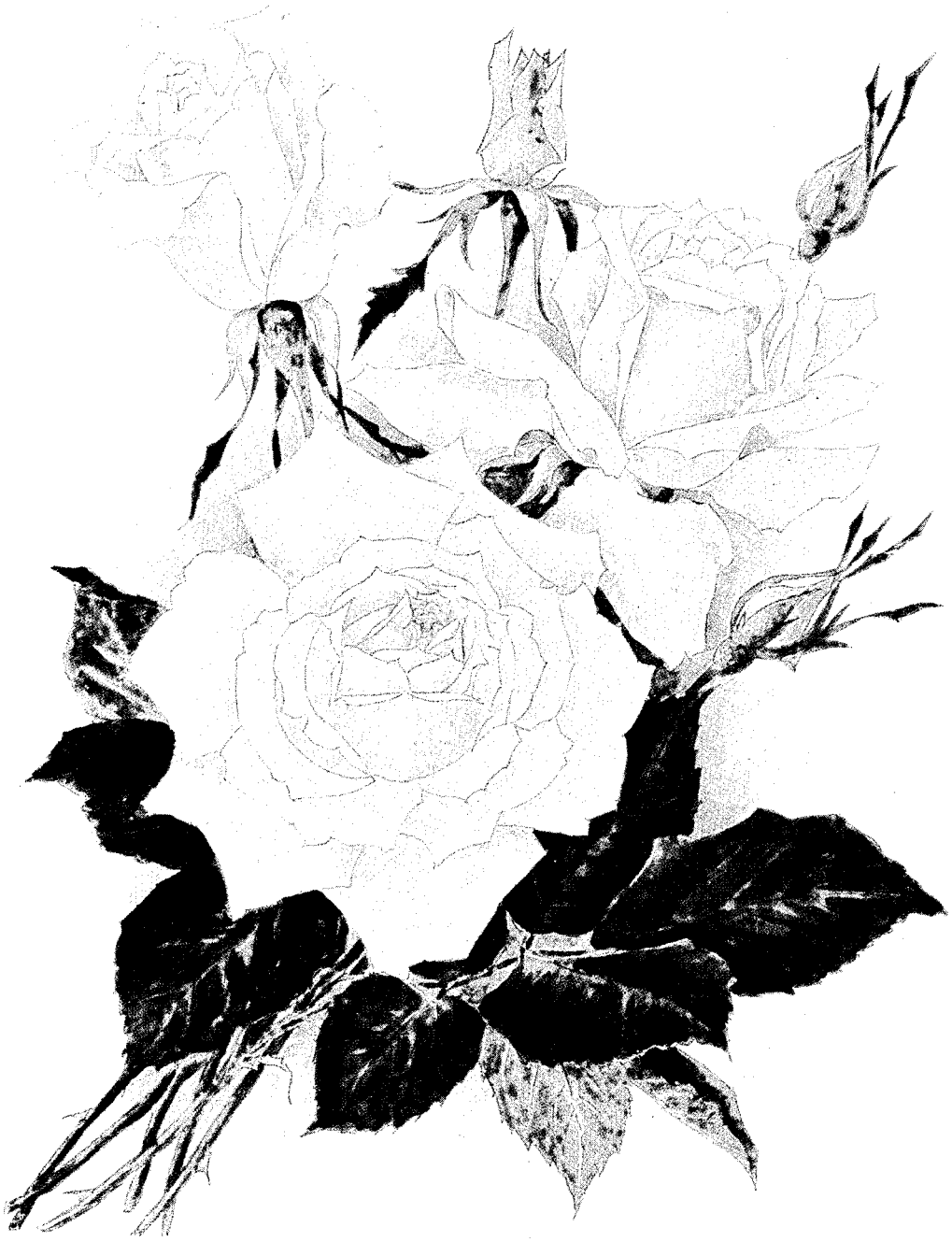
Witness
Addison E. Avery
Eugene R. Dramm
by Rummler, Rummler
& Woodworth Patented Nov. 1, 1938 Plant Pat. 301

UNITED STATES PATENT OFFICE

301

ROSE

Eugene R. Dramm, Elmhurst, Ill., assignor to Dramm Greenhouse, Inc., Elmhurst, Ill., a corporation of Illinois Application February 14, 1938, Serial No. 190,363

1 Claim. (Cl. 47—61)

This patent specification is directed to a rose plant distinguishable from others which are most closely related thereto mainly by the color, form, fragrance, size of the bloom and by the petal form. The closely related plants referred to are descendants of the Hybrid Tea rose "Columbia", such as the "Briarcliff" and "Better Times", the latter of which is described in Plant Patent No. 23. "Columbia" is referred to in Plant Patent No. 254.

The improved rose herein disclosed is a sport of "Better Times" and somewhat more like "Columbia" than "Better Times", although decisively varying from each. The color of the rose, Geranium Pink or Bermuda, is approximately intermediate between that of "Columbia" and "Better Times", being decidedly lighter than "Better Times" and having definitely more depth than "Columbia". Without reference to a color chart, an artist might ordinarily designate the color by saying it is a moderate pink slightly modified by a purplish orchid cast.

A characteristic of the improved rose is that of the general uniformity of its blooms; that is without noticeable difference in color or size of individual blooms of the same crop and substantially the same age.

These characteristics of the bloom are reliable and apparently fixed as experienced through approximately three years of careful attention to the growth of many thousands of plants grafted onto "Manetti" stock.

The new rose is believed to have desirable characteristics in the novel general tonal effect en masse, the free, large development of the bloom, leathery texture of the petals and a rich, noticeable and agreeable rose fragrance.

The original painting from which the accompanying reduced illustration is made, is true to size, form and petalage of the natural bloom and also gives approximately the same general color tone when viewed at a distance of a few feet.

The original sport occurred on one plant of a large number of "Better Times" plants which were growing in the Dramm Greenhouses at Elmhurst, Illinois, approximately three years ago. Since that time production of the new rose has been rapidly increased, exclusively in the same greenhouses and none has been grown outdoors. At the present time something over 2,400 plants are growing of this rose and 10,000 to 15,000 newly grafted plants are potted.

In growth and habits, the new rose is somewhat similar to "Better Times" but is hardier and stronger and the petalage is more double. The growth is also more vigorous, the bloom more prolific and more uniform in size and color. The petals also differ from the parent rose in being more definitely pointed at the tips centrally of the longitudinal axis of the petal and this pointed form is accentuated by the curling back of the petal at each side of its tip. The pronounced tip to each petal is also apparent in the smaller central petals.

The partly opened bloom is urn-shaped having a compact mass of petals. There are between 50 and 60 petals to a bloom. The stems have more thorns than the "Better Times" and the thorns are rather large, unequally spaced and hooked downwardly.

This new variety is particularly valuable for use as a cut flower because of its deep uniform Geranium Pink color, excellent keeping qualities (both on the bush and when cut), the size of the blossoms, and all-year round profusion of blossoms.

The following is a more complete description of the plant and flower of this new variety:

Sport of "Better Times".

Length of time of propagation: since the spring of 1935.

*The flower*

Blooming habit:
Remontant—very prolific.

Bud:
*Size.*—About 1½ inches in height.
*Form.*—Short, conical type.
*Calyx.*—Normal.
*Sepals.*—Cover bud.

Bloom:
*Size.*—About 4½ inches across when fully open.
*Borne.*—Singly.
*Opens.*—Uniformly.
*Stems.*—Strong, heavy, rigid.
*Form.*—Urn-shaped.
*Petalage.*—50 to 60; very double, thick and leathery; evenly arranged and of nearly equivalent size; convolute when fully developed.
*Color.*—Geranium Pink shading into Salvia.
*Discoloration.*—Outer whorl of petals becomes a little lighter in color about the 4th day but the center holds its deep, clear tone.
*Texture.*—Leathery.
Not affected by wet or hot weather.
*Persistence.*—Petals hang on very well and drop off clean about 7th day.
*Fragrance.*—Noticeable and agreeable.

Genital organs:
Enclosed in calyx. Covered by petals until blossom has fully opened.

*Plant*

Disease resistant.

Form:
Bush.

Growth:
18 to 21 inches without pinching.

Foliage:

*Quantity.*—Plentiful, averaging 3 to 5 leaflets on the rachises.

*Size.*—Mature leaflets about 2½ or 3 inches.

*Shape.*—Acute, margin sharply but not deeply serrated.

Thorns:

Stout, hooked—quite thorny.

*Color chart*

(According to A Dictionary of Color by Maerz & Paul)

| | Color | Plate | Letter | No. |
|---|---|---|---|---|
| Base of petal | Chartreuse | 11 | L | 1 |
| Shading into | | 9 | E | 6 |
| Do | | 1 | A | 5 |
| Lighter section of body of rose. | Geranium Pink; Bermuda. | 1 | J | 8 |
| Shading into darker section of body. | | 1 | G | 6 |
| Very center or heart of blossom. | Salvia | 3 | L | 6 |
| Extreme edge of large petals. | | 1 | A | 3 |
| Buds: | | | | |
| Base of petals in small buds. | Asphodel Green. | 21 | J | 5 |
| Lighter section of small bud petals. | Zinnia | 4 | L | 2 |
| Shading to | Oxheart | 6 | L | 5 |
| Inside of sepals | Water Green | 19 | C | 2 |
| Outside of sepals | | 20 | L | 7 |
| Tip of sepals | | 24 | L | 6 |
| Calyx | | 20 | L | 8 |
| Body of leaf | | 24 | L | 6 |
| Lighter streak at midrib and base of veins. | Peridot | 22 | L | 6 |
| Under side of leaf | Willow+ | 15 | L | 7 |
| Small stem of leaves | Ivy Green | 16 | L | 9 |
| Stem | Calla Green | 22 | L | 4 |
| Thorns | | 14 | L | 5 |

In habit, the new variety of rose has some of the characteristics of its progenitor, "Columbia", of which "Better Times" back to "Briarcliff" were sports. In color it is similar to "Columbia" but more intense. Like "Briarcliff" it is expected it will do well out-of-doors in the summer as the petalage is so very double; but up to this time it has been grown only in the greenhouse.

In a full-blown rose, from the second verticil of the outer petals toward the center, the corolla is urn-shaped with the petals closely bunched and of uniform color. As the blossom fully opens, the petals curl back gracefully in a decidedly triangular form, and it is only then that the pistils and stamens show. At this full-blown stage, the rose resembles a peony. The peduncles are strong and rigid, thus permitting the flower to open fully without drooping.

This new variety of rose is uniform in color and does not fade readily. It holds its color and very full center until the petals begin to drop off. The average production of bloom per year to a plant is from 20 to 25 blossoms.

When these roses are put into a bouquet, their most striking characteristics are their uniform, large size and gorgeous coloring.

I claim:

The herein described rose, a sport of Hybrid Teas and distinguishable from others of the same class by its substantially uniform Geranium Pink color, leathery texture of petals, centrally pointed at the outer edge and curled back from the point and thus producing a somewhat angular petal outline, and further characterized by a rich, pleasing fragrance, uniformity of size and color, strong rigid stems, profusion of blooms, very double petalage, and clean healthy growth.

EUGENE R. DRAMM.